United States Patent [19]

Stock

[11] Patent Number: 5,098,409
[45] Date of Patent: Mar. 24, 1992

[54] INTRAVENOUS BAG AND MONITORING METHOD

[75] Inventor: Elisabeth A. Stock, Scarsdale, N.Y.

[73] Assignee: Massachusetts Institute of Technology, Cambridge, Mass.

[21] Appl. No.: 637,453

[22] Filed: Jan. 4, 1991

[51] Int. Cl.$^5$ .............................................. A61M 5/00
[52] U.S. Cl. ................................ 604/246; 604/260; 128/DIG. 12; 128/DIG. 13
[58] Field of Search .................. 604/253, 254, 65–67, 604/153, 245, 246, 260, 118, 247, 185; 128/DIG. 12, DIG. 13; 340/591, 592, 603, 605, 618

[56] References Cited

U.S. PATENT DOCUMENTS

| | | | |
|---|---|---|---|
| 1,219,723 | 3/1917 | Gracey et al. | 340/91 |
| 1,816,464 | 7/1931 | Biggert | 33/501.04 |
| 3,151,616 | 10/1964 | Selfon | 604/131 |
| 3,640,277 | 2/1972 | Adelberg | 604/141 |
| 3,690,318 | 9/1972 | Gorsuch | 604/141 |
| 3,884,228 | 5/1975 | Hahn | 604/131 |
| 3,942,526 | 3/1976 | Wilder et al. | 604/253 |
| 3,992,706 | 11/1976 | Tunney et al. | 340/618 |
| 4,079,736 | 3/1978 | Lundquist | 604/52 |
| 4,176,349 | 11/1979 | Fliegel | 340/613 |
| 4,204,538 | 5/1980 | Cannon | 604/246 |
| 4,277,226 | 7/1981 | Archibald | 417/38 |
| 4,496,351 | 1/1985 | Hillel et al. | 604/250 |
| 4,530,696 | 7/1985 | Bisera et al. | 604/253 |

FOREIGN PATENT DOCUMENTS 2400192  4/1979  France .............................. 62/403

*Primary Examiner*—C. Fred Rosenbaum
*Assistant Examiner*—Manuel Mendez
*Attorney, Agent, or Firm*—Hamilton, Brook, Smith & Reynolds

[57] ABSTRACT

An intravenous bag monitoring device is connected between an IV bag which holds fluid to be delivered to a patient and a hollow IV needle which is injected into a vein of a patient. The monitoring device comprises a chamber, an inlet leading to the chamber, and an outlet leading away from the chamber. A corrugated flexible wall panel is positioned in the chamber and divides the chamber into a first section which contains fluid and a second section which does not contain fluid. A spring is positioned in the second section of the chamber. The movement of the flexible wall panel in response to changes in hydrostatic force is resisted by the spring. An elongated push rod is attached to the flexible wall, passes through the second section and forms one of two contacts required to complete a warning circuit. The other contact is on the exterior of the second chamber. As the IV bag fluid flows to the patient, the hydrostatic force in the chamber decreases causing the flexible wall panel to draw the push rod further into the chamber. A predetermined period of time before the IV bag empties a predetermined hydrostatic force threshold is reached, at which time the electrical contact on the end of the push rod outside of the chamber wall touches the electrical contact on the chamber wall. Thus, the warning circuit is completed and a signal indicating that the bag is almost empty is generated.

20 Claims, 1 Drawing Sheet

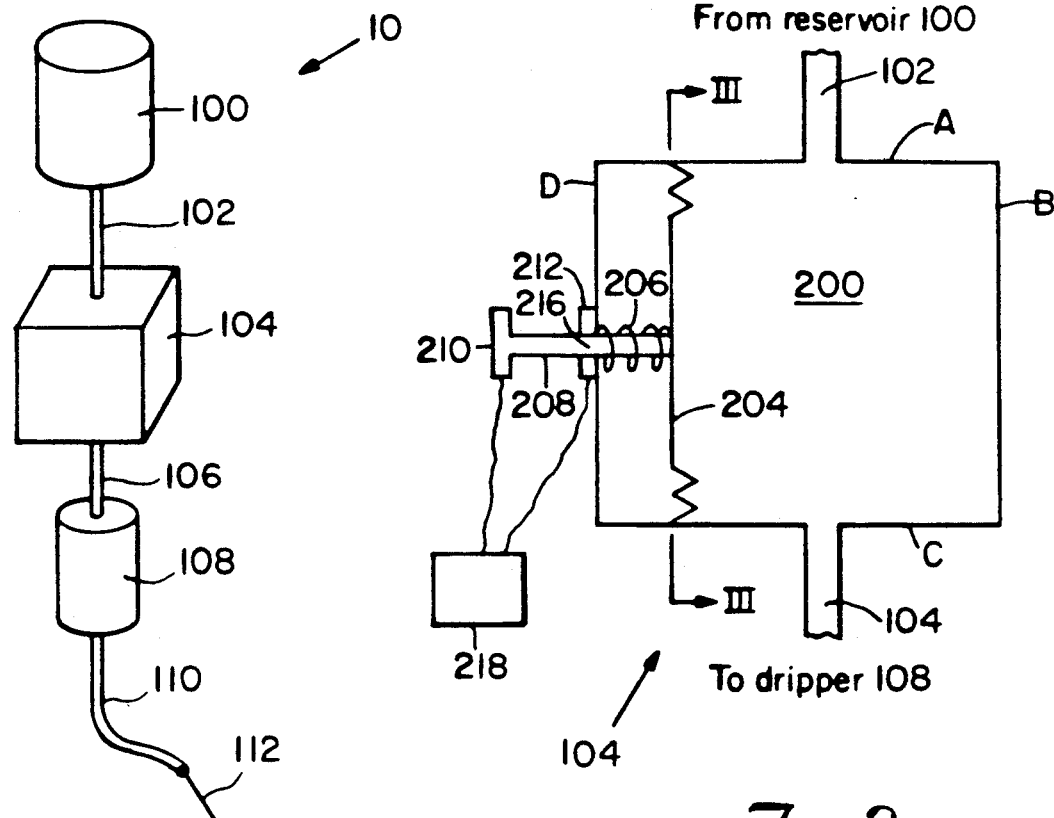
Fig. 1
Fig. 2
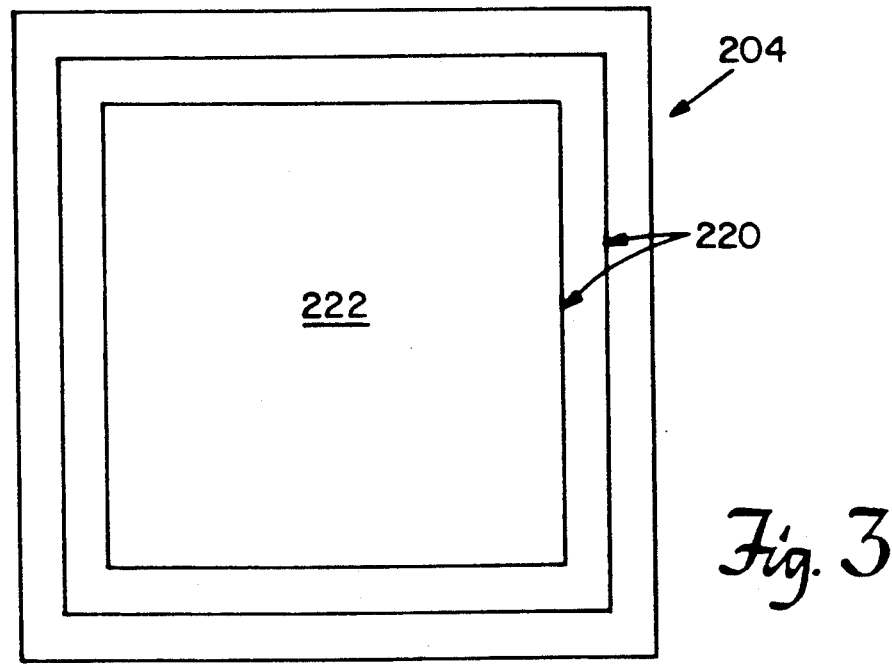
Fig. 3

INTRAVENOUS BAG AND MONITORING METHOD

BACKGROUND OF THE INVENTION

The intravenous infusion of fluids into a patient's bloodstream is a common medical procedure. Fluids that are typically administered intravenously include glucose and saline solutions, drugs, and blood. Intravenous (IV) systems generally comprise a reservoir, a dripper, a feed tube, and an IV needle. The reservoir, also called an IV bag, holds a quantity of the fluid to be infused. The reservoir is coupled to a dripper by means of a feed tube. The dripper, in turn, is coupled by the feed tube to the hollow IV needle, which is injected into a vein of the patient. The fluid in the reservoir drips by gravity flow through the needle and into the bloodstream, with the drip rate being controlled by the dripper.

It is imperative that an IV system be carefully monitored for a number of reasons. First, since the fluids that are administered are often life-maintaining solutions, such as drug solutions, the reservoir must never be allowed to empty for prolonged periods. Harmful or even fatal consequences may otherwise result. In addition, if the IV system runs out of fluid, blood will flow back from the patient and clot inside the needle. If this happens, the needle must be replaced by a new needle, with the replacement procedure being painful for the patient and time-consuming for the hospital staff. Hence, the IV system requires frequent inspection by the hospital staff. However, the shortages of qualified staff and high costs characterizing hospitals today make it difficult to administer such thorough patient care.

As a result, several types of devices to automatically monitor the amount of fluid remaining in an IV system have been developed. One group of devices makes use of a scale mechanism, such as a seesaw. When the amount of remaining fluid falls below some predetermined value, the seesaw tilts and actuates an electrical switch to trigger an alarm. Although these scale-based devices are simple, the springs used in the scales are quite sensitive to jolts or shocks that can occur, for example, if the patient accidentally strikes the device.

Another type of prior art device makes use of a clip or clamp together with elements that complete an electrical signalling circuit as the reservoir bag collapses on emptying. The chief disadvantage of such clamp-based devices are that the clamp can affect the rate of flow of the IV fluid and that the alerting signal is only activated when the reservoir is empty, as opposed to it being nearly empty.

Still another prior art device uses optical sensing equipment to sense the fluid level of the dripper and to monitor the IV for occlusion or bubbles in the fluid. Here, the disadvantage lies in the complexity and high cost of such equipment.

SUMMARY OF THE INVENTION

Therefore, a need exists for an IV monitoring device that provides an alert signal when a predetermined low level of fluid remains in the IV system. Such a device should not be sensitive to external shock. In addition, the device should be inexpensive, and preferably, disposable, to avoid the need for between-use cleaning.

The invention comprises an apparatus for monitoring fluid from an IV reservoir by coupling the reservoir to a chamber having an inlet, an outlet and a flexible wall. An interior wall of the reservoir is flexible. Fluid from the IV reservoir flows through the chamber. A spring contacts the chamber flexible wall and resists the hydrostatic force applied on the opposite side of the flexible wall. A sensor responsive to the spring generates an output signal when the hydrostatic force is less than a predetermined level which indicates that the IV reservoir will be empty in a predetermined period of time. A warning circuit connected to the sensor generates an empty IV bag warning signal in response to the sensor output signal.

In the preferred embodiment, the sensor comprises first and second electrical contacts. The contacts touch when the hydrostatic force is below said predetermined level. The invention provides a simple, efficient, and inexpensive apparatus for preventing IV fluid cutoff in advance of total IV fluid depletion.

The above and other features of the invention including various novel details of construction and combinations of parts will now be more particularly described with reference to the accompanying drawings and pointed out in the claims. It will be understood that the particular device embodying the invention is shown by way of illustration and not as a limitation of the invention. The principles and features of this invention may be employed in varied and numerous embodiments without departing from the scope of the invention.

BRIEF DESCRIPTION OF THE DRAWINGS

FIG. 1 is a schematic perspective view of a typical intra-venous system equipped with the monitoring device of the present invention.

FIG. 2 is a cross-sectional schematic of the bag monitoring device of the invention.

FIG. 3 is a plan view of the flexible wall of the monitoring device.

DETAILED DESCRIPTION OF THE INVENTION

The IV bag monitoring device of the present invention will now be described in connection with FIGS. 1 and 2. FIG. 1 is a schematic of a typical IV system 10 equipped with a monitoring device of the invention. The system comprises in general a fluid reservoir 100, feed tubes 102, 106, 110, monitoring device 104, dripper 108, and a hollow IV needle 112. The reservoir 100, also called an IV bag 100, holds a quantity of the fluid to be delivered to the patient. The reservoir 100 is coupled to the top of the bag monitor 104 by means of a feed tube 102. The bottom of the bag monitor 104 is connected by feed tube 106 to the top of the dripper 108. The bottom of the dripper 108 is in turn coupled by feed tube 110 to a hollow IV needle 112, which is injected into a vein of the patient (not shown in FIG. 1). The fluid in the reservoir 100 drips by gravity flow through the bag monitor 104, the dripper 100, and finally the needle 112 and into the bloodstream, with the drip rate being controlled by the dripper 108.

The bag monitoring device 104 of the invention, shown in FIG. 2, may be made of rigid plastic or other similar IV fluid compatible material. A cubic exterior shape is shown for bag monitoring device 104. However, the bag monitoring device may be of any shape.

An inlet tube 102 from the reservoir 100 allows fluid to flow into chamber 200 of the bag monitoring device 104. Fluid drains from chamber 200 through tube 106. A flexible plastic interior wall panel 204 divides chamber 200 into a first section to the right of panel 204 which contains fluid and a second section to the left of panel 204 which does not contain fluid. Interior wall panel 204 is illustrated in FIG. 3. The exterior periphery of wall panel 204 has a series of concentric square corrugations 220 which make the panel flexible in the sense that it can move in or out depending on the hydrostatic forces in the first section of the chamber. In other words, the corrugations 220 allow the central portion 222 of the interior wall panel 204 to flex in response to changes in the hydrostatic force. The central portion 222 of the interior wall panel 204 and the corrugations 204 may also be circular in shape. The chamber 200 can be constructed by first forming the exterior wall portions of the first section of chamber 200 which will contain fluid. As shown in FIG. 2, wall B, and portions of walls A and C which extend to the interior wall panel 204 form part of the exterior of monitor 104. The flexible interior wall panel 204 is attached to the fluid holding first section of chamber 200 by sealing the outer periphery of panel 204 to the walls of A, C, inter alia, of monitor 104. Finally, the second section of the chamber comprising wall D and the parts of walls A and C to the left of interior wall panel 204 (as shown in FIG. 2) are sealed to the periphery of panel 204.

The flexible interior wall panel 204 functions as a diaphragm which moves in response to changes in the hydrostatic force in the fluid containing first section of chamber 200. The hydrostatic force is resisted by a helical spring 206 which extends from the central portion of the square interior wall panel 204 to the central portion of wall D of monitor 104. An elongated push rod 208 having a distal end and a proximal end is attached to the central portion of the interior wall panel 204. Epoxy or a similar substance is used to connect the distal end of push rod 208 to panel 204. The elongated body of the push rod 208 is coaxial with the helical spring 206 in the second section of chamber 200 which does not contain fluid. The elongated body of the push rod 208 exits the chamber 200 at an aperture 216 in the wall D of the monitor 104. A first electrical contact 212 surrounds aperture 216. The proximal end of push rod 208 comprises a second electrical contact 210. As will be explained in detail below, electrical contacts 210 and 212 form a switch which will open and close in response to changes in the hydrostatic force in chamber 200. When electrical contacts 210 and 212 are touching, a signal is activated in warning circuit 218.

During normal operation, i.e., when the IV bag 100 is nearly full, fluid flows by gravity flow from the IV bag 100 into the chamber 200 of the bag monitor 104 through the inlet 102. Simultaneously, fluid flows out the feed tube 106 to the dripper 108. Since the IV bag has fluid inside, the bag monitor chamber 200 remains filled. As a consequence, a hydrostatic force is exerted on the panel 204 by the fluid in the chamber 200, thereby pushing the panel 204 outward and to the left in FIG. 2.

This action is countered by spring 206 coiled around push rod 208 between panel 204 and wall D. Rod 208 is coupled to the panel 204 by epoxy and extends through an aperture 216 in wall D. The spring constant of the spring 206 is sufficient, when the reservoir 200 is full, to prevent contact 210 at the end of push rod 208 from contacting contact 212 bonded to wall D of chamber 200.

However, when the IV bag becomes empty, the fluid in chamber 200 begins to empty. As this occurs, the hydrostatic force exerted on the panel 204 is decreased. Consequently, the spring 206 expands and panel 204 moves inward. As the diaphragm moves inward, electrical contact 210 moves closer to electrical contact 212. Once the fluid level in the reservoir 200 is sufficiently low, the contacts 210 and 212 touch, thereby activating warning circuit 218 which produces an audible or other type alarm.

The specifics of the construction, which determine when the electrical signal is actuated, are now described in the following example. In this embodiment, the bag monitor reservoir 200 is cubic in shape, with side lengths chosen to be 3.6 cm. The volume of the bag monitor reservoir is thus $(3.6 cm)^3 = 46.7$ cc. The specific example will transmit the electrical warning signal 10 minutes prior to the emptying of fluid in the IV system 10.

In order to accommodate the worst case, in which IV fluid can flow through the IV system at a maximum rate of 3.33 cc/min, there must be (3.33 cc/min) (10 min) = 33.3 cc of fluid in the system Since the dripper reservoir 108 has a capacity of 10 cc, the alarm should be triggered when the bag monitor reservoir 200 has 33.3 cc − 10 cc = 23.3 cc of fluid in it. Equivalently, the alarm should be triggered when the bag monitor reservoir is half-full (half of 46.7 cc is 23.3 cc).

To accomplish this, the spring constant k of the spring 206 is chosen so that the force exerted by the spring equals the hydrostatic force of the fluid exerted on the diaphragm 204 when there are 23.3 cc of fluid in the bag monitor reservoir. Assuming an IV bag height of 5 cm, the hydrostatic pressure is given by:

$$P_h = \rho g h = (10^3 \text{ kg/m}^3)(10 \text{ m/sec}^2)(0.05 \text{ m}) = \frac{500 \text{ kg}}{\text{m} - \text{sec}^2},$$

where $\rho$ denotes the density of the IV fluid and is assumed to be roughly that of water. The hydrostatic pressure $P_h$ and hydrostatic force $F_h$ are related by $$P_h = \frac{F_h}{A}$$

where A denotes the area of the diaphragm 204 and is equal to $(3.6 \text{ cm})^2 = 13.0 \text{ cm}^2$. Hence $$F_h = P_h A = \left(\frac{500 \text{ kg}}{\text{m} - \text{sec } 2}\right)(0.0013 \text{ m}^2) = 6.5 \text{ N}.$$

The spring force is given by:

$$F_s = kx,$$

where X denotes the distance that the spring 206 has been compressed. Arbitrarily choosing X to be 1 cm and setting $F_s$ equal to $F_h$ yields:

$$k = \frac{6.5 \text{ N}}{0.01 \text{ m}} = 650 \text{ N/M}$$

Equivalents

Those skilled in the art will recognize, or be able to ascertain, using no more than routine experimentation, many equivalents to the specific embodiments of the invention described herein.

These and all other equivalents are intended to be encompassed by the following claims.

I claim:

1. An apparatus for monitoring fluid from an IV reservoir having a first outlet tube comprising:
   a chamber having a flexible wall, an inlet and an outlet, said chamber inlet connected to said IV reservoir first outlet tube,
   a second outlet tube connected to said chamber outlet and adapted to be connected to an IV needle,
   a spring contacting the flexible wall of the chamber and applying a force thereto,
   a sensor for generating an output signal when the hydrostatic force is less than a predetermined level which indicates that the IV reservoir will be empty in a predetermined period of time, and
   a warning circuit, connected to said sensor, which will generate an empty IV bag warning signal in response to said sensor output signal.

2. An apparatus, as recited in claim 1, wherein the sensor further comprises a first and a second electrical contact such that said contacts touch when the hydrostatic force is below said predetermined level.

3. An apparatus, as recited in claim 1, wherein the chamber volume is substantially constant.

4. An apparatus, as recited in claim 3, wherein the flexible wall is corrugated.

5. An apparatus, as recited in claim 1, wherein the spring is helical and contacts a central portion of the flexible wall.

6. An apparatus for monitoring fluid from an IV reservoir comprising:
   an IV reservoir for delivering IV fluid to a patient;
   a first tube with a proximal end and a distal end, said first tube proximal end connected to the IV bag;
   a bag monitor, including a chamber with an inlet and an outlet and a flexible panel responsive to the hydrostatic force in the chamber, said chamber inlet connected to said first tube distal end;
   an empty IV bag warning circuit responsive to said flexible panel, for generating a warning signal a predetermined period of time before the IV bag empties; and
   a second tube with a proximal end and a distal end, said second tube proximal end connected to said chamber outlet, said second tube distal end adapted to be connected to an IV needle.

7. An apparatus, as recited in claim 6, wherein said flexible panel divides the chamber into a first section which contains fluid and a second section which does not contain fluid.

8. An apparatus, as recited in claim 7, wherein the bag monitor further comprises:
   a spring, positioned in the chamber second section to resist the hydrostatic force acting on the flexible panel;
   an elongated rod with a distal and proximal end, said rod distal end coupled to the flexible panel, said rod exits the chamber second section at an aperture in the chamber;
   a first electrical contact on the chamber exterior near the aperture; and
   a second electric contact on the rod proximal end, such that when the predetermined hydrostatic force occurs in the chamber, the first and second electrical contacts connect and activate the empty IV bag warning circuit to generate an empty IV bag warning signal.

9. An apparatus, as recited in claim 8, wherein the chamber is cubic in shape.

10. An apparatus, as recited in claim 8, wherein the flexible panel is corrugated in shape.

11. An apparatus, as recited in claim 10, wherein the flexible panel is further comprised of plastic.

12. An apparatus, as recited in claim 8, wherein the spring is helical in shape.

13. An apparatus as recited in claim 12 wherein the rod is coaxial with the helical spring.

14. An apparatus, as recited in claim 8 wherein the chamber is further comprised of plastic.

15. An apparatus as recited in claim 6 further comprising a dripper with an inlet and an outlet, said dripper inlet connected to said second tube distal end, and a third tube with a distal end and a proximal end, said third tube proximal end connected to said dripper outlet, said third tube distal end adapted to be connected to an IV needle.

16. An apparatus for monitoring an IV bag fluid comprising:
   (a) an IV bag for delivering fluid to a patient;
   (b) a first tube with a proximal end and a distal end, said first tube proximal end connected to the IV bag;
   (c) a bag monitor, coupled to the first tube, including
   (i) a chamber having an inlet and an outlet;
   (ii) a flexible panel, said flexible panel divides the chamber into a first section containing fluid and a second section without fluid;
   (iii) a helical spring, said spring positioned between said flexible panel in the chamber second section to resist the hydrostatic force in the chamber;
   (iv) an elongated rod with a distal and proximal end and coaxial with the helical spring, said rod distal end coupled to the flexible panel, said rod exits the chamber second section at an aperture in the chamber wall;
   (v) an electrical warning circuit;
   (vi) a first electrical contact on the chamber exterior near the aperture; and
   (vii) a second electric contact on the rod proximal end, such that when the predetermined hydrostatic force occurs in the chamber, the first and second electrical contacts connect and activate the electrical warning circuit to generate an empty IV bag warning signal a predetermined period of time before the IV bag empties.

17. A method for monitoring fluid from an IV reservoir flowing from a tube connected to the IV reservoir comprising:
   passing the fluid from the tube through a chamber having a flexible wall;
   applying force to the exterior of the flexible wall;
   generating an empty IV bag warning signal a predetermined period of time before the IV bag empties when the hydrostatic force in the reservoir falls below a predetermined threshold.

18. An apparatus for monitoring fluid from an IV reservoir coupled to an IV needle comprising:
   a chamber with a diaphragm formed in a wall the interior of said chamber in fluid communication with the reservoir and the IV needle,
   a sensor responsive to movement of the diaphragm for generating an output signal when the hydrostatic force on the diaphragm is less than a predetermined amount which indicates that the IV reservoir will be empty in a predetermined period of time, and for generating a warning signal when the force exceeds the amount.

19. An apparatus, as recited in claim 18, wherein the sensor comprises a spring contacting the diaphragm and first and second electrical contacts responsive to the spring such that said contacts touch when the hydrostatic force is below said predetermined level.

20. An apparatus, as recited in claim 19, wherein the diaphragm comprises an interior flexible side wall of said chamber.

* * * * *